(12) United States Patent
Deemer

(10) Patent No.: US 8,686,176 B2
(45) Date of Patent: Apr. 1, 2014

(54) SYNTHESIS OF REVERSIBLY PROTECTED SILANES

(75) Inventor: Michael F. Deemer, Pulaski, OH (US)

(73) Assignee: University of Akron Research Foundation, Akron, OH (US)

( * ) Notice: Subject to any disclaimer, the term of this patent is extended or adjusted under 35 U.S.C. 154(b) by 0 days.

(21) Appl. No.: 13/279,547

(22) Filed: Oct. 24, 2011

(65) Prior Publication Data
US 2012/0116098 A1    May 10, 2012

Related U.S. Application Data

(60) Provisional application No. 61/410,986, filed on Nov. 8, 2010.

(51) Int. Cl.
*C07F 7/04* (2006.01)
*C07D 309/04* (2006.01)

(52) U.S. Cl.
USPC .......................................... 556/471; 549/214

(58) Field of Classification Search
USPC .......................................................... 549/214
See application file for complete search history.

(56) References Cited

U.S. PATENT DOCUMENTS

| | | | |
|---|---|---|---|
| 7,022,803 B2 | 4/2006 | Bowen et al. | 528/32 |
| 7,034,171 B2 | 4/2006 | Bowen et al. | 556/51 |
| 7,034,175 B2 | 4/2006 | Bowen et al. | 556/446 |
| 7,053,162 B2 | 5/2006 | Bowen et al. | 526/279 |
| 7,057,060 B2 | 6/2006 | Bowen et al. | 556/446 |
| 7,060,773 B2 | 6/2006 | Bowen et al. | 526/279 |
| 7,067,600 B2 | 6/2006 | Bowen et al. | 526/279 |
| 7,074,866 B2 | 7/2006 | Bowen et al. | 526/279 |
| 7,078,471 B2 | 7/2006 | Bowen et al. | 526/279 |
| 7,078,549 B2 | 7/2006 | Bowen et al. | 556/446 |
| 7,084,226 B2 | 8/2006 | Bowen et al. | 526/279 |
| 7,084,289 B2 | 8/2006 | Bowen et al. | 556/446 |
| 7,109,281 B2 | 9/2006 | Bowen et al. | 526/279 |

FOREIGN PATENT DOCUMENTS

EP    1437357 A1    7/2004

*Primary Examiner* — Rebecca Anderson
*Assistant Examiner* — Karen Cheng
(74) *Attorney, Agent, or Firm* — Alvin T. Rockhill

(57) ABSTRACT

The present invention discloses a method for synthesizing a reversibly protected organometallic compound which comprises (1) reacting an organometallic compound with a hydroxyl group containing compound to produce a solution containing the reversibly protected organometallic compound and hydrogen chloride; (2) reacting the solution containing the reversibly protected organometallic compound and the hydrogen chloride with a trialkyl amine to precipitate the hydrogen chloride from the solution; and (3) recovering the reversibly protected organometallic compound from the solution of the reversibly protected organometallic compound.

20 Claims, No Drawings

SYNTHESIS OF REVERSIBLY PROTECTED SILANES

This application claims benefit of U.S. Provisional Patent Application Ser. No. 61/410,986, filed on Nov. 8, 2010. The teachings of U.S. Provisional Patent Application Ser. No. 61/410,986 are incorporated herein by reference in their entirety.

BACKGROUND OF THE INVENTION

Reversibly protected silanes can be used for diverse purposes in a wide variety of applications. The development of reversible protecting groups greatly enhances the current utility of silanes while making novel new applications possible. For instance, reversibly protected silanes are of particular value in applications where room temperature cure and/or adhesion is of value, such as coatings, high resolution imaging, caulks, adhesives, sealents, gaskets, and silicones. Reversibly protected silanes can also be beneficially used in reticulating agents, and in sizing agents, tires, and release coatings.

The incorporation of reversibly protected silanes into coating resins is of particular value. Reversibly protected silanes can be incorporated into coating resins by polymerizing a monomer containing the reversibly protected silane into the resin or by post-addition into the coating formulation. The reversibly protected silane remains protected under basic conditions, such as in a coating formulation that contains a volatile base, for instance ammonium hydroxide. However, deprotection occurs under mildly acidic conditions. Thus, as a coating formulation containing a volatile base dries the volatile base evaporates and deprotection occurs. This allows for controlled room temperature crosslinking to occur with hydroxy-functionalized polymers. Chemical adhesion to hydroxy-group containing substrates, such as metal, glass, and wood, also occurs. This makes coating resins that contain reversibly protected silanes especially valuable for coating metals, glass, and wood. Since such coating formulations that contain reversibly protected silanes are curable at room temperature they are much easier to apply and cure than conventional systems. Benefits associated with using coating formulations that contain reversibly protected silanes are realized in a wide variety of applications including structural coatings, anti-corrosion coatings, and marine biofouling coatings.

U.S. Pat. No. 7,022,803 relates to the synthesis of a latex which can be used in making self-crosslinking water-reducible coating compositions, such as paints, which offer excellent solvent resistance, reduced drying time and improved adhesion to metal and glass. Coatings which are formulated with the latex of U.S. Pat. No. 7,022,803 are environmentally advantageous because they contain no or extremely low levels of volatile organic compounds and additionally offer excellent flexibility and excellent ultra-violet light resistance. This patent more specifically discloses a water-reducible coating composition which is comprised of (1) water; (2) a resin having repeat units which are derived from (a) about 30 to about 75 weight percent vinyl aromatic monomers, (b) about 20 to about 65 weight percent of alkyl acrylate monomers, (c) about 1 to about 8 weight percent alkyl propenoic acid monomers and (d) about 0.5 to about 5 weight percent reversibly protected silane monomers, based on 100 weight percent monomers; (3) a wetting agent; and (4) a defoamer.

U.S. Pat. No. 7,022,803 further discloses a modified silane compound having a structural formula selected from the group consisting of

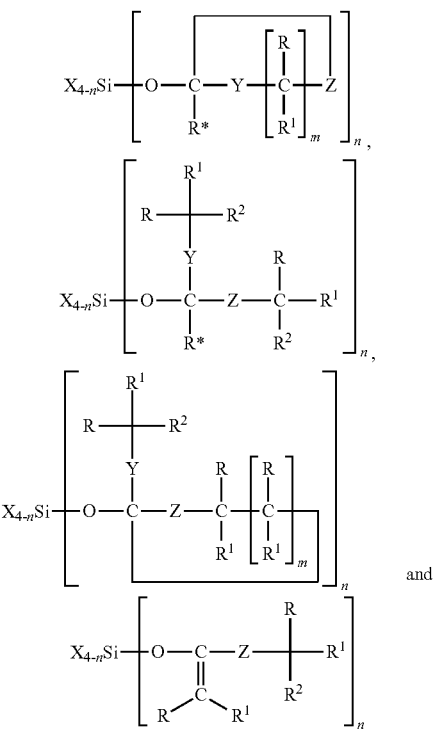

wherein n represents an integer from 2 to 4; wherein m represents an integer from 1 to about 20; with the proviso that m can represent the integer 0 for structures of formula (3) wherein Z represents the group $C(R)R^1$; wherein X groups can be the same or different; wherein X represents a chemical moiety; with the proviso that X does not represent a methyl group, an ethyl group, or a phenyl group in cases where the modified silane compound is of structural formula (2) wherein n represents the integer 1 or the integer 2 wherein R* represents a hydrogen atom wherein Y represents an oxygen atom wherein Z represents the moiety $C(R)R'$; wherein $R, R^1$, and $R^2$ can be the same or different and are selected from the group consisting of hydrogen atoms, alkyl groups containing from 1 to about 12 carbon atoms, aryl groups containing from about 6 to about 18 carbon atoms, alkaryl groups containing from 7 to about 18 carbon atoms, alkoxy groups containing from 1 to about 18 carbon atoms, hydroxy groups, and halide atoms; wherein R* is selected from the group consisting of hydrogen atoms, alkyl groups containing from 1 to about 12 carbon atoms, aryl groups containing from about 6 to about 18 carbon atoms, and alkaryl groups containing from 7 to about 18 carbon atoms; wherein $R, R^1, R^2$, and R* can be bonded together in any combination in cases where $R, R^1, R^2$, and R* are not hydrogen atoms, halide atoms, or hydroxy groups; wherein Y represents a moiety selected from the group consisting of $C(R)R'$, oxygen, sulfur, nitrogen, and phosphorus; wherein Z represents a moiety selected from the group consisting of $C(R)R^1$, oxygen, sulfur, nitrogen, and phosphorus; with the proviso that Y and Z can not both represent the moiety $C(R)R^1$; wherein the contiguous cyclic ring in formulas (1) and (3) can contain heteroatoms selected from the group consisting of oxygen, sulfur, nitrogen, phosphorus, and silicon in cases where m represents an integer greater than 1; wherein the contiguous cyclic ring in formulas (1) and (3) can be saturated or unsaturated in cases where m represents an integer greater than 1; wherein said alkyl groups, aryl groups, alkaryl groups, and alkoxy groups can contain halide atoms and heteroatoms selected from the group consisting of oxygen, sulfur, nitrogen, phosphorus, and silicon. Modified silanes of these types and similar monomers are also disclosed in U.S. Pat. Nos. 7,034,171, 7,034,175, 7,053,162, 7,057,060, 7,060,773, 7,067,600, 7,074,866, 7,078,471, 7,078,549, 7,084,226, 7,084,289, and 7,109,281.

The above-listed patents disclose synthesis techniques for making reversibly protected silanes. However, these techniques can result in gel formation, the presence of residual hydrogen chloride, and/or require expensive starting materials. In any case, a simple, low cost synthesis technique for preparing reversibly protected silanes which are free of undesirable reaction by-products on a commercial basis is needed.

SUMMARY OF THE INVENTION

The present invention provides a simple, low cost synthesis technique for preparing reversibly protected organometallic compound, including reversibly protected silanes, that are free of undesirable reaction by-products which can easily be implemented on a commercial basis. This process can be carried out at moderate temperatures without the need for utilizing extremely low temperatures. It is also more commercially viable because the raw materials utilized do not require extraordinary operating conditions or handling. For instance, this process does not require sodium hydride as is needed in conducting some prior art techniques.

The present invention more specifically discloses a method for synthesizing a reversibly protected organometalic compound, such as a reversibly protected silane, which comprises (1) reacting an organometalic compound of the structural formula: $A_x$-$MX_y$ or $X_3M$-$A$-$MX_3$ with a hydroxyl group containing compound having a formula selected from the group consisting of:

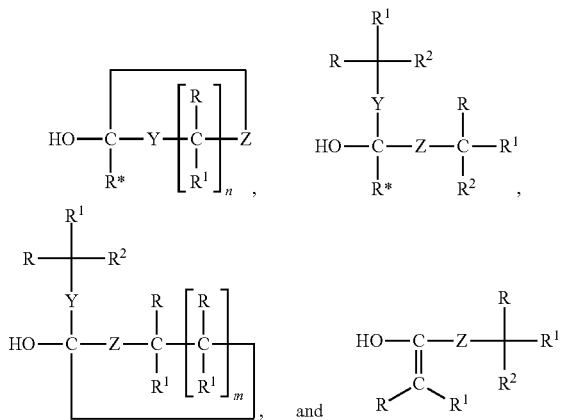

wherein M represents a member selected from the group consisting of silicon, germanium, tin, lead, titanium, hafnium, and zirconium; wherein A represents a hydrocarbyl moiety; wherein X represents a halogen atom; wherein x and y represent integers from 1 to 3; wherein the sum of x and y is 4; wherein n represents an integer from 1 to about 20; wherein m represents an integer from 0 to 20; wherein Z represents a group —$C(R)(R^1)$—; wherein R, $R^1$, and $R^2$ can be the same or different and are selected from the group consisting of hydrogen atoms, alkyl groups containing from 1 to about 12 carbon atoms, aryl groups containing from about 6 to about 18 carbon atoms, alkaryl groups containing from 7 to about 18 carbon atoms, alkoxy groups containing from 1 to about 18 carbon atoms, hydroxy groups, and halide atoms; wherein R* is selected from the group consisting of hydrogen atoms, alkyl groups containing from 1 to about 12 carbon atoms, aryl groups containing from about 6 to about 18 carbon atoms, and alkaryl groups containing from 7 to about 18 carbon atoms; wherein R, $R^1$, $R^2$, and R* can be bonded together in any combination in cases where R, $R^1$, $R^2$, and R* are not hydrogen atoms, halide atoms, or hydroxy groups; wherein Y represents a moiety selected from the group consisting of —$C(R)(R^1)$—, oxygen, sulfur, nitrogen, and phosphorus; wherein Z represents a moiety selected from the group consisting of —$C(R)(R^1)$, oxygen, sulfur, nitrogen, and phosphorus; with the proviso that Y and Z can not both represent the moiety —$C(R)(R^1)$—; wherein the silane is reacted with the hydroxyl group containing compound in an organic solvent at a temperature of less than about 100° C. to produce a solution containing the reversibly protected organometalic compound and hydrogen chloride; (2) reacting the solution containing the reversibly protected organometalic compound and the hydrogen chloride with a trialkyl amine to precipitate the hydrogen chloride from the solution to produce a solution of the reversibly protected organometalic compound; and (3) recovering the reversibly protected organometalic compound from the solution of the reversibly protected organometalic compound.

DETAILED DESCRIPTION OF THE INVENTION

The technique of this invention can be used in synthesizing a wide variety of reversibly protected silanes including the reversibly protected silanes described in U.S. Pat. No. 7,022,803, 7,034,171, 7,034,175, 7,053,162, 7,057,060, 7,060,773, 7,067,600, 7,074,866, 7,078,471, 7,078,549, 7,084,226, 7,084,289, and 7,109,281. The teachings of U.S. Pat. No. 7,022,803, 7,034,171, 7,034,175, 7,053,162, 7,057,060, 7,060,773, 7,067,600, 7,074,866, 7,078,471, 7,078,549, 7,084,226, 7,084,289, and 7,109,281 are incorporated hereby by reference for the purpose of teaching reversibly protected silanes that can be made utilizing the method of this invention.

In the first step of the process of this invention, an organometallic compound of the structural formula $A_x$-$MX_y$ is reacted with a certain type of hydroxyl group-containing compound. In the organometallic compound of the structural formula $A_x$-$MX_y$, the M represents a member selected from the group consisting of silicon, germanium, tin, lead, titanium, hafnium, and zirconium. M typically represents silica in which case the organometallic compound is of the formula: $A_x$-$SiX_y$. For purposes of this invention, the compounds of the formula $A_x$-$MX_y$ are referred to as organometallic compounds even though it is appreciated from a technical standpoint that in cases where M represents silicon that they are silanes rather than being organometallic compounds as they are in cases where M represents germanium, tin, lead, titanium, hafnium, or zirconium. However, for purposes of simplicity in cases where M represents silicon the compound is still referred to as being an organometallic compound even though it does not contain a metal.

In the structural formula $A_x$-$MX_y$, the A group represents a hydrocarbyl moiety which will typically contain from 1 to 30 carbon atoms which can be aromatic or aliphatic. The A group will more typically contain from about 6 to about 15 carbon atoms and can also optionally contain heteroatoms, such a silicon atom. In cases where monomeric reversibly protected silanes are being synthesized the A group will be a hydrocarbyl moiety that contains at least one non-aromatic double bond. In such cases, it is preferred for the A group to contain only one non-aromatic double bond which can be in the backbone of the A group or which can be present in the form of a pendant vinyl group. In various embodiments of this invention the A group can be of a formula selected from the group consisting of:

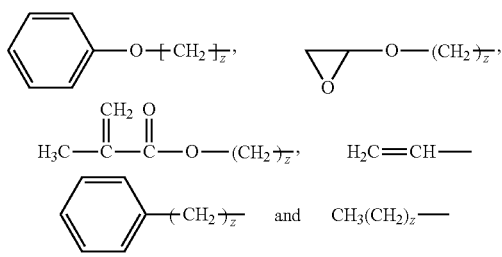

wherein z represents an integer from 1 to 12. In such compounds it is more typical for z to represent an integer which is within the range of 2 to 8. For instance, z can be 2, 3, 4, or 5. In the case where the A group includes a silicon atom, the A group can be of the formula: $—(CH_2)_z—SiCl_3$, wherein z again represents an integer from 1 to 12 with z typically representing an integer from 2 to 8.

In the silane of the structural formula $A_x$-$MX_y$ the X represents a halogen which is typically chlorine, fluorine, bromine, or iodine. It is typical for X to represent chlorine. In this formula x and y both represent integers within the range of 1 to 3 where the some of x and y is 4. In most cases x will represent 1 and y will represent 3. For instance, the silane can be of the formula: $A-MCl_3$.

The hydroxyl group containing compound will typically be of a formula selected from the group consisting of:

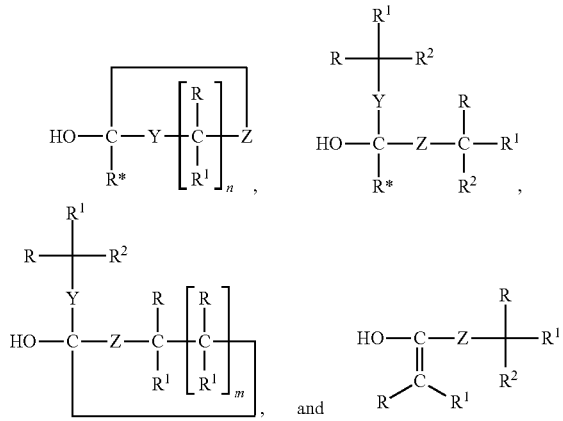

wherein A represents a hydrocarbyl moiety; wherein X represents a halogen atom; wherein x and y represent integers from 1 to 3; wherein the sum of x and y is 4; wherein n represents an integer from 1 to about 20; wherein m represents an integer from 0 to 20; wherein Z represents a group $—C(R)(R^1)—$; wherein R, $R^1$, and $R^2$ can be the same or different and are selected from the group consisting of hydrogen atoms, alkyl groups containing from 1 to about 12 carbon atoms, aryl groups containing from about 6 to about 18 carbon atoms, alkaryl groups containing from 7 to about 18 carbon atoms, alkoxy groups containing from 1 to about 18 carbon atoms, hydroxy groups, and halide atoms; wherein R* is selected from the group consisting of hydrogen atoms, alkyl groups containing from 1 to about 12 carbon atoms, aryl groups containing from about 6 to about 18 carbon atoms, and alkaryl groups containing from 7 to about 18 carbon atoms; wherein R, $R^1$, $R^2$, and R* can be bonded together in any combination in cases where R, $R^1$, $R^2$, and R* are not hydrogen atoms, halide atoms, or hydroxy groups; wherein Y represents a moiety selected from the group consisting of $—C(R)(R^1)—$, oxygen, sulfur, nitrogen, and phosphorus; wherein Z represents a moiety selected from the group consisting of $—C(R)(R^1)$, oxygen, sulfur, nitrogen, and phosphorus; with the proviso that Y and Z can not both represent the moiety $—C(R)(R^1)—$.

The hydroxyl group containing compound will frequently be of the formula:

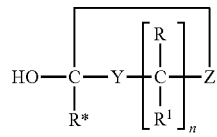

wherein Y represents an oxygen atom, wherein R and $R^1$ represent hydrogen atoms, wherein n represents 3, wherein x represents 1 and wherein y represents 3. In such a scenario the hydroxyl group containing compound will be of the formula:

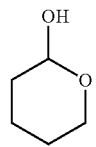

In the first step of the method of this invention the silane will typically be reacted with the hydroxyl group containing compound at a temperature of 100° C. or less. This reaction will more typically be conducted at a temperature which is within the range of 0° C. to 60° C. and will preferably be conducted at a temperature which is within the range of 10° C. to 40° C. To maintain a desired reaction temperature the reactor containing the reactants can be maintained in a cooling bath, such as ice water. This step of the reaction is typically carried out at atmospheric pressure. However, it is possible to also conduct the reaction at an elevated pressure to inhibit boiling of the solvent system. In another scenario, the reaction could also be carried out under reduced pressure. However, there is no benefit associated with utilizing reduced pressures. This reaction will normally be conducted in an inert organic solvent. The inert organic solvent which is utilized will typically be a hydrocarbon which is liquid at ambient temperatures which can be one or more aromatic, paraffinic or cycloparaffinic compounds. These solvents will normally contain from 4 to 10 carbon atoms per molecule and will be liquids under the conditions of the reaction. It is, of course, important for the solvent selected to be inert. The term "inert" as used herein means that the solvent does not interfere with the reaction or react with the reversibly protected silane made thereby. Some representative examples of suitable organic solvents include diethyl ether, tetrahydrafuran, pentane, isooctane, cyclohexane, normal hexane, benzene, toluene, xylene, ethylbenzene and the like, alone or in admixture. It is typically preferred to utilize a mixed hexanes solvent system. It should be appreciated the solvent system should be void of alcohols because alcohols can lead to unwanted side reactions.

The first step of the synthesis technique of this invention results in the formation of a solution containing the reversibly protected silane and hydrogen chloride. In the second step of the process of this invention, a trialkyl amine is added to the solution containing the reversibly protected silane and the hydrogen chloride to precipitate the hydrogen chloride from the solution to produce a solution of the reversibly protected silane which is essentially free of hydrogen chloride. The second step can be carried out concurrently with the first step by including the trialkyl amine in the reaction medium or it can be carried out as a subsequent step by simply adding the trialkyl amine to the solution made in the first step of the process. It should further be noted that it can be commercially advantageous to continuously carry out the precipitation to remove the hydrogen chloride in a side vessel. This could be carried out by removing the hydrogen chloride with the nitrogen flow into a side vessel wherein the precipitation takes place. The trialkyl amine chloride can then be recovered and used in other applications or sold as a separate raw material for utilization in a multitude of other industries, including pharmaceuticals. The trialkyl amine used in this step of the process will typically have an alkyl group that contains from 1 to about 8 carbon atoms and will more typically have alkyl groups that contain from 1 to about 4 carbon atoms, such as triethyl amine. The precipitate can then be removed from the solvent by filtration, decantation, centrifugation, or the like to recover a solution of the reversibly protected silane in the solvent.

The solution containing the reversibly protected silane can then be passed through a column of drying agent, such as magnesium sulfate, to remove any water that may be present. Then, the reversibly protected silane can be recovered from the purified solution by evaporating the solvent or by distillation.

This invention is illustrated by the following examples that are merely for the purpose of illustration and are not to be regarded as limiting the scope of the invention or the manner in which it can be practiced. Unless specifically indicated otherwise, parts and percentages are given by weight.

EXAMPLE 1

The procedure used in this experiment can be depicted by the reaction:

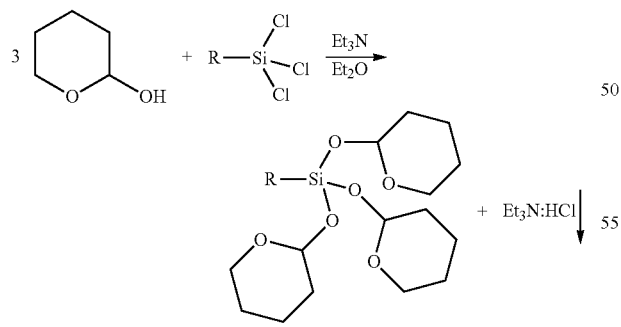

In the procedure used all glassware was cleaned, rinsed with acetone, and dried in an oven. Then, under a nitrogen stream, diethyl ether, 3.3 molar ratio 2-hydroxytetrahydropyran, and 6 molar ratio of triethyl amine were added to a reaction flask. More specifically 6.4 grams of 2-hydroxytetrahydropyran and 11.3 grams of triethylamine in approximately 70 ml of dry diethyl ether were added to the flask. Then, diethyl ether and 1 mole of a trichlorosilane were added to an addition funnel under a nitrogen stream. Specifically, 5.0 grams of 3-phenoxypropyltrichlorosilane in approximately 20 ml of dry diethyl ether were added. The diethyl ether/chlorosilane solution was added dropwise over 60 minutes with the solution being continually mixed.

The solution was then filtered under nitrogen. The filtrate was mixed another hour and filtered as necessary. The filtrate was placed in a separatory funnel. The filtrate was washed with 10% HCl until the pH of the aqueous phase was within the range of 4 to 5 (as determined using pH paper). After washing and extracting the aqueous phase, the organic phase was passed through a column containing magnesium sulfate to remove any water. The dried organic phase was then distilled to remove the diethyl ether to recover the protected 3-phenoxypropylsilane reaction product shown below.

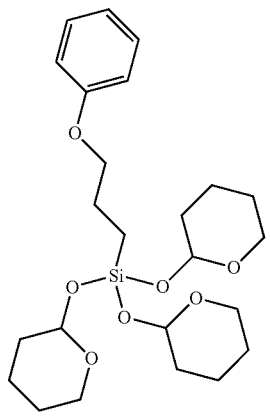 [SMILES: c1ccc(OCCC[Si](OC2CCCCO2)(OC2CCCCO2)OC2CCCCO2)cc1]

While certain representative embodiments and details have been shown for the purpose of illustrating the subject invention, it will be apparent to those skilled in this art that various changes and modifications can be made therein without departing from the scope of the subject invention.

What is claimed is:

1. A method for synthesizing a reversibly protected organometallic compound or a reversibly protected silane which comprises (1) reacting an organometallic compound of the structural formula: $A_x\text{-}MX_y$ with a hydroxyl group containing compound having a formula selected from the group consisting of:

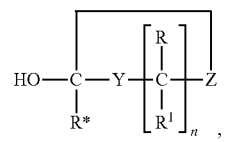

wherein M represents a member selected from the group consisting of silicon, germanium, tin, lead, titanium, hafnium, and zirconium; wherein A represents an unsaturated hydrocarbyl moiety containing at least one non-aromatic double bond; wherein X represents a halogen atom; wherein x and y represent integers from 1 to 3; wherein the sum of x and y is 4; wherein n represents an integer from 1 to about 20; wherein Z represents a group —C(R)(R$^1$)—; wherein R and R$^1$ can be the same or different and are selected from the group consisting of hydrogen atoms, alkyl groups containing from 1 to about 12 carbon atoms, aryl groups containing from about 6 to about 18 carbon atoms, alkaryl groups containing from 7 to about 18 carbon atoms, alkoxy groups containing from 1 to about 18 carbon atoms, hydroxy groups, and halide atoms; wherein R* is selected from the group consisting of hydrogen atoms, alkyl groups containing from 1 to about 12 carbon atoms, aryl groups containing from about 6 to about 18 carbon atoms, and alkaryl groups containing from 7 to about 18 carbon atoms; wherein R, $R^1$, and R* can be bonded together in any combination in cases where R, $R^1$, and R* are not hydrogen atoms, halide atoms, or hydroxy groups; wherein Y represents a moiety selected from the group consisting of —C(R)($R^1$)—, oxygen, sulfur, nitrogen, and phosphorus; wherein Z represents a moiety selected from the group consisting of —C(R)($R^1$), oxygen, sulfur, nitrogen, and phosphorus; with the proviso that Y and Z cannot both represent the moiety —C(R)($R^1$)—; wherein the organometallic compound is reacted with the hydroxyl group containing compound in an organic solvent at a temperature of less than about 100° C. to produce a solution containing the reversibly protected organometallic compound and hydrogen chloride; (2) reacting the solution containing the reversibly protected organometallic compound and the hydrogen chloride with a trialkyl amine to precipitate the hydrogen chloride from the solution to produce a solution of the reversibly protected organometallic compound, wherein step (2) can be carried out concurrently with step (1) or subsequently to step (1); and (3) recovering the reversibly protected organometallic compound from the solution of the reversibly protected organometallic compound.

2. The method as specified in claim 1 wherein M represents silicon.

3. The method as specified in claim 2 wherein R* represents a hydrogen atom.

4. The method as specified in claim 3 wherein Y represents an oxygen atom.

5. The method as specified in claim 4 wherein R and $R^1$ represent hydrogen atoms.

6. The method as specified in claim 5 wherein n represents 3.

7. The method as specified in claim 6 wherein x represents 1 and wherein y represents 3.

8. The method as specified in claim 7 wherein X represents chlorine.

9. The method as specified in claim 1 wherein the trialkyl amine has alkyl groups that contain from 1 to 4 carbon atoms.

10. The method as specified in claim 1 wherein the trialkyl amine is triethyl amine.

11. The method as specified in claim 1 wherein the reaction of step (1) is conducted at a temperature which is within the range of about 0° C. to about 60° C.

12. The method as specified in claim 2 wherein step (1) and step (2) are conducted simultaneously.

13. A method for synthesizing a reversibly protected silane which comprises (1) reacting an organometallic compound of the structural formula: $A_{x-M}X_y$ with a hydroxyl group containing compound having a formula selected from the group consisting of:

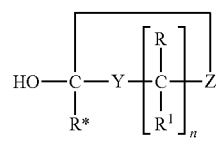

wherein M represents silicon; wherein A has a structural formula selected from the group consisting of:

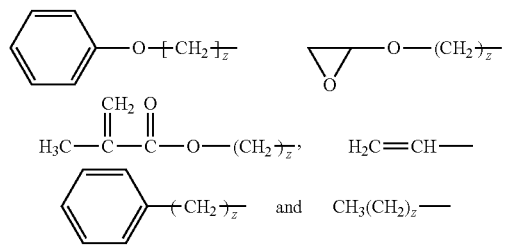

wherein z represents an integer from 1 to 12; wherein X represents a halogen atom; wherein x and y represent integers from 1 to 3; wherein the sum of x and y is 4; wherein n represents an integer from 1 to about 20; wherein Z represents a group —C(R)($R^1$)—; wherein R and $R^1$ can be the same or different and are selected from the group consisting of hydrogen atoms, alkyl groups containing from 1 to about 12 carbon atoms, aryl groups containing from about 6 to about 18 carbon atoms, alkaryl groups containing from 7 to about 18 carbon atoms, alkoxy groups containing from 1 to about 18 carbon atoms, hydroxy groups, and halide atoms; wherein R* is selected from the group consisting of hydrogen atoms, alkyl groups containing from 1 to about 12 carbon atoms, aryl groups containing from about 6 to about 18 carbon atoms, and alkaryl groups containing from 7 to about 18 carbon atoms; wherein R, $R^1$, and R* can be bonded together in any combination in cases where R, $R^1$, and R* are not hydrogen atoms, halide atoms, or hydroxy groups; wherein Y represents a moiety selected from the group consisting of —C(R)($R^1$)—, oxygen, sulfur, nitrogen, and phosphorus; wherein Z represents a moiety selected from the group consisting of —C(R)($R^1$), oxygen, sulfur, nitrogen, and phosphorus; with the proviso that Y and Z cannot both represent the moiety —C(R)($R^1$)—; wherein the organometallic compound is reacted with the hydroxyl group containing compound in an organic solvent at a temperature of less than about 100° C. to produce a solution containing the reversibly protected organometallic compound and hydrogen chloride; (2) reacting the solution containing the reversibly protected organometallic compound and the hydrogen chloride with a trialkyl amine to precipitate the hydrogen chloride from the solution to produce a solution of the reversibly protected organometallic compound, wherein step (2) can be carried out concurrently with step (1) or subsequently to step (1); and (3) recovering the reversibly protected organometallic compound from the solution of the reversibly protected organometallic compound.

14. The method as specified in claim 13 wherein A represents a group of the formula:

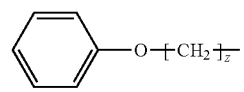

wherein z represents an integer from 1 to 12.

15. The method as specified in claim 14 wherein z represents 3.

16. A method for synthesizing a reversibly protected silane which comprises (1) reacting an organometallic compound of the structural formula: $A_x$-$MX_y$ with a hydroxyl group containing compound having a formula selected from the group consisting of:

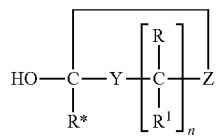

wherein M represents silicon; wherein A is of the formula: —$(CH_2)_z$—$SiCl_3$, wherein z represents an integer from 1 to 12; wherein X represents a halogen atom; wherein x and y represent integers from 1 to 3; wherein the sum of x and y is 4; wherein n represents an integer from 1 to about 20; wherein Z represents a group —$C(R)(R^1)$—; wherein R and $R^1$ can be the same or different and are selected from the group consisting of hydrogen atoms, alkyl groups containing from 1 to about 12 carbon atoms, aryl groups containing from about 6 to about 18 carbon atoms, alkaryl groups containing from 7 to about 18 carbon atoms, alkoxy groups containing from 1 to about 18 carbon atoms, hydroxy groups, and halide atoms; wherein R* is selected from the group consisting of hydrogen atoms, alkyl groups containing from 1 to about 12 carbon atoms, aryl groups containing from about 6 to about 18 carbon atoms, and alkaryl groups containing from 7 to about 18 carbon atoms; wherein R, $R^1$, and R* can be bonded together in any combination in cases where R, $R^1$, and R* are not hydrogen atoms, halide atoms, or hydroxy groups; wherein Y represents a moiety selected from the group consisting of —$C(R)(R^1)$—, oxygen, sulfur, nitrogen, and phosphorus; wherein Z represents a moiety selected from the group consisting of —$C(R)(R^1)$, oxygen, sulfur, nitrogen, and phosphorus; with the proviso that Y and Z cannot both represent the moiety —$C(R)(R^1)$—; wherein the organometallic compound is reacted with the hydroxyl group containing compound in an organic solvent at a temperature of less than about 100° C. to produce a solution containing the reversibly protected organometallic compound and hydrogen chloride; (2) reacting the solution containing the reversibly protected organometallic compound and the hydrogen chloride with a trialkyl amine to precipitate the hydrogen chloride from the solution to produce a solution of the reversibly protected organometallic compound, wherein step (2) can be carried out concurrently with step (1) or subsequently to step (1); and (3) recovering the reversibly protected organometallic compound from the solution of the reversibly protected organometallic compound.

17. The method as specified in claim 13 wherein R* represents a hydrogen atom.

18. The method as specified in claim 17 wherein Y represents an oxygen atom.

19. The method as specified in claim 18 wherein R and $R^1$ represent hydrogen atoms.

20. The method as specified in claim 19 wherein n represents 3.

* * * * *